United States Patent [19]
Byrne et al.

[11] Patent Number: 6,074,380
[45] Date of Patent: Jun. 13, 2000

[54] DEVICE AND METHOD FOR TRANSCUTANEOUS SURGERY

[75] Inventors: Phillip Owen Byrne, Newcastle-upon-tyne; Thomas Stuart Jackson Elliott, Sutton Coldfeld, both of United Kingdom

[73] Assignee: BTG International Limited, London, United Kingdom

[21] Appl. No.: 09/037,087

[22] Filed: Mar. 9, 1998

Related U.S. Application Data

[63] Continuation of application No. PCT/GB96/02263, Sep. 12, 1996.

[30] Foreign Application Priority Data

Sep. 15, 1995 [GB] United Kingdom ................ 9518888

[51] Int. Cl.⁷ .................................................. A61M 5/32
[52] U.S. Cl. ........................... 606/1; 606/108; 604/27; 604/174; 604/175; 604/177
[58] Field of Search ......................... 604/158, 93, 21, 604/27, 174, 175, 177, DIG. 26; 606/108, 1

[56] References Cited

U.S. PATENT DOCUMENTS

| | | |
|---|---|---|
| 1,351,917 | 9/1920 | Kuhn . |
| 4,062,363 | 12/1977 | Bonner ........................ 128/349 |
| 4,080,970 | 3/1978 | Miller .......................... 604/174 |
| 4,400,169 | 8/1983 | Stephen ......................... 604/93 |
| 4,820,264 | 4/1989 | Matsui et al. ................ 604/174 |
| 5,123,402 | 6/1992 | Vandensbossche et al. ..... 128/7 |
| 5,211,644 | 5/1993 | Van Beek et al. .............. 606/1 |
| 5,368,575 | 11/1994 | Chang ......................... 604/175 |
| 5,417,656 | 5/1995 | Ensminger et al. ............ 604/93 |
| 5,417,666 | 5/1995 | Coulter ....................... 604/172 |
| 5,554,106 | 9/1996 | Layman-Spillar et al. .... 604/175 |
| 5,713,858 | 2/1998 | Heruth et al. ................ 604/175 |
| 5,713,859 | 2/1998 | Finch, Jr. et al. ............. 604/93 |
| 5,728,103 | 3/1998 | Picha et al. .................. 604/174 |
| 5,836,914 | 11/1998 | Houghton ..................... 604/117 |

FOREIGN PATENT DOCUMENTS 2140 695 12/1984 United Kingdom .
93/14809 8/1993 WIPO .......................... A61M 35/00

OTHER PUBLICATIONS

Wai–Kin Lin et al: "The effect of electric current on bacteria colonising intravenous catheters", Journal of Infection (1993)27 pp. 261–269, (see Appln p. 2).

within alleged knowledge of IPEA Examiner: A perfume funnel, being a small cup–shaped, i.e. shallow funnel with a tubular distal extension which is used for pouring perfume from a larger bottle into a small flacon. (See IPER sheet 3–4; no specific document cited).

*Primary Examiner*—Linda C. M. Dvorak
*Assistant Examiner*—Sonya Harris- Ogugua
*Attorney, Agent, or Firm*—Pillsbury Madison & Sutro LLP

[57] ABSTRACT

This invention relates to a device and method for use in transcutaneous surgical procedures, such as transcutaneous catheterization and surgical biopsy.

To provide that the operative parts of instrumentation to be introduced into the patient's body are shielded from contact with the patient's skin, and thereby to inhibit transfer of micro-organisms from the skin into the body, there is provided a transcutaneous indwelling shield device for insertion into a skin aperture, comprising a transcutaneous distal portion providing an instrument access port, connecting to a proximal portion of shallow dished form of substantially greater dimension than said access port, the proximal portion tapering inwardly to said distal portion to readily guide the distal tip of the instrument to said access port. The distal portion serves as a wound retractor, and to this end at least the distal portion may be of resilient form to be resiliently deformed from a first, relatively open, configuration to a second, relatively closed, configuration.

The invention has particular application in the field of central venous catheterization.

11 Claims, 3 Drawing Sheets

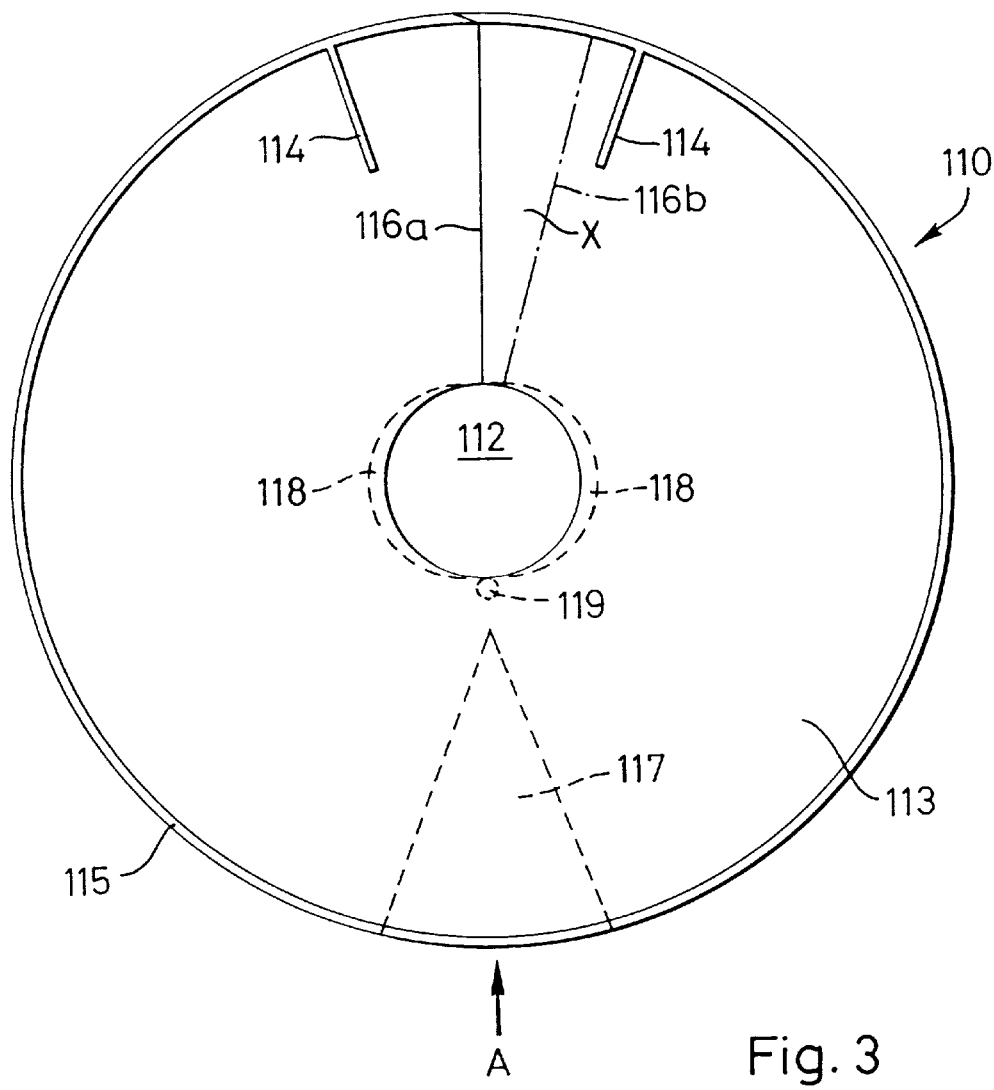
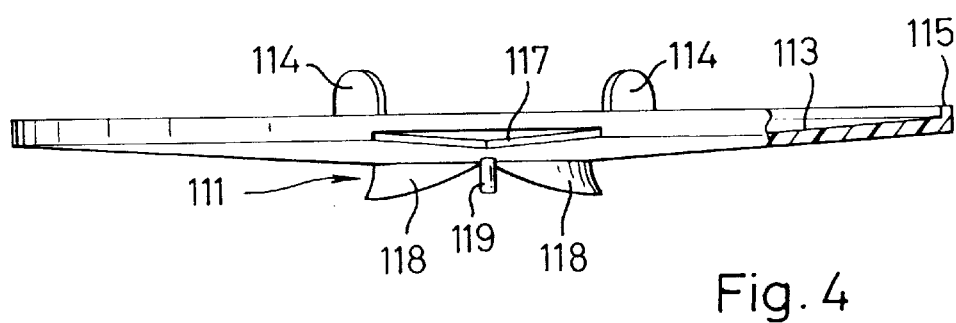
Fig. 3
Fig. 4

DEVICE AND METHOD FOR TRANSCUTANEOUS SURGERY

This is a Continuation of International Appln. No. PCT/GB96/02263 filed Sep. 12, 1996 which designated the U.S.

This invention relates to a device and method for use in transcutaneous surgical procedures, such as transcutaneous catheterisation and surgical biopsy. A particular area of interest is that of central venous catheterisation.

In a central venous catheterisation procedure, a catheter is inserted directly into the circulatory system via a transcutaneous incision. The catheter can be advanced to a desired position within the circulatory system, and once in place allows continuous and accurate monitoring of cardiovascular conditions, such as the patient's blood pressure. Such monitoring permits detection of dangerous haemodynamic events during patient therapy and surgery. For example, to measure right atrial pressure the catheter must be advanced to a position in a major vein within the chest or directly in the right atrium.

In a typical central venous catheterisation procedure the first step is the preparation of a suitable entrance site by wiping the surrounding area of skin with an antiseptic swab. Such a site may be, for example, in the leg (femoral), arm (brachial) or neck (carotid/jugular) of the patient. The surgeon then makes a small scalpel incision in the skin of (say) 10–20 mm in length (although smaller or larger incisions will be appropriate in the case of some surgical procedures), and uses a hollow needle to locate the blood vessel through which the catheter is to be introduced. A strong, flexible guidewire is then introduced through the lumen of the hollow needle and into the vessel, the needle is removed and the guidewire is advanced to the target site under control guidance using standard imaging techniques to monitor the progress of the guidewire tip. For a femoral entry to access a cardiac site, the guidewire may extend for a meter or more within the patient's body.

The next step in the procedure is to dilate the perforation in the vascular wall to accommodate the subsequent introduction of the catheter. For this purpose at least one hollow dilator is used, which takes the form of a shaped cylindrical body with a central bore and an external diameter selected to be marginally greater than the existing diameter of the vascular aperture. The dilator is passed over the guidewire, the central bore being sized to accommodate the diameter of the guidewire, and is manipulated by the surgeon to impact the wall of the incision and of the vascular aperture in order to widen said aperture.

A series of dilators of progressively increasing diameter (eg. successively increasing in steps of 1 mm) may be used in sequence to enlarge the aperture until the appropriate size is reached, when the final dilator is removed. The next step of the procedure is the introduction of the catheter, which is provided with a central bore of greater diameter than that of the guidewire and which can therefore readily be fed onto and along the guidewire, the distal tip being advanced to the target site. Finally the guidewire can be removed through the catheter and the catheter can be connected to a monitoring device, such as a pressure monitoring system. Depending on the therapy involved, the catheter may remain indwelling for up to 72 hours, or in some cases even longer.

One of the most serious problems in the procedure outlined above and in the use of transcutaneous procedures in general is the problem of infection. Although the scalpel, needle, guidewire, dilator(s) and catheter are sterile (and are usually disposable single-use items), each component is likely to come into contact with the skin before coming into contact with the blood vessel. The initial skin preparation is only partially effective as it removes only superficial bacteria, and micro-organisms which remain can therefore readily be transferred from the skin in the area of the incision to internal sites, leading to sepsis.

This problem is recognised in the journal article "The effects of electric current on bacteria colonising intravenous catheters" by Wal-Kin Liu et al, Journal of Infection (1993) 27, 261–269. The authors make mention of the fact that between 4 and 18% of all central venous catheters are associated with sepsis, most usually caused by coagulase-negative staphylococci. The associated micro-organisms are derived primarily from patients' skin, some gaining access to the catheter at the time of insertion, others migrating along the outer surface of the catheter while it is indwelling. The article outlines several approaches to the prevention of central venous catheter infection, including improved catheter care, modification of the properties of the polymers used, use of antimicrobial agents, and the effect of direct electric current.

More recent study by the present inventors into the source of micro-organisms involved the investigation of 30 patients undergoing open heart surgery, all of whom had triple lumen 30 cm central venous catheters inserted immediately prior to surgery. The skin was prepared using a chlorhexidine/alcohol swab and rigorous aseptic precautions were taken. Various components of the introduction sets were subsequently assessed for contamination using standard microbiological techniques. The following table shows the results of this assessment:

| Component | No. Tested | No. Contaminated |
| --- | --- | --- |
| Scalpel | 14 | 2 |
| Insertion needle | 30 | 9 |
| Guidewire | 30 | 15 |
| Dilator | 29 | 14 |
| CVC distal tips | 30 | 5 |

The CVC distal tips were subjected to in situ sampling, by passing them through a cellulose acetate membrane which was then placed onto a blood agar plate for incubation.

The study concludes that micro-organisms, present on the skin and within the stratum corneum even after disinfection, are impacted onto the various components as they are introduced, so transferring contamination into the patient's internal system. In particular, 18% of the catheter distal tips assessed in the study have impacted organisms immediately after insertion.

The general question of reduction in infection in catheterisation procedures is addressed in U.S. Pat. No. 5,417,666. This document discloses a sterile shield for use in catheterisation of the human urethra, and involves the insertion of a cylindrical semi-rigid funnel member with a removable cover member into the urethra to a depth greater than the extent of contamination. The cover member is then removed and a catheter can be inserted through the funnel member to reach the patient's bladder without coming into contact with contaminated parts of the urinary tract. Although devices of this sort are useful in maintaining sterility in simple medical procedures involving insertion through natural body orifices, there presently exists no device for satisfactorily preventing contamination in transcutaneous operations, particularly in situations in which a number of instruments are to be used in successive manner, and the likelihood of contact with the surrounding skin area is therefore significantly increased.

It is an object of the present invention to reduce the risk of contamination of components used in transcutaneous procedures, and to this end according to the invention there is provided a transcutaneous shield device for insertion into a skin aperture, comprising a transcutaneous distal portion providing an instrument access port, connecting to a proximal portion of shallow dished form of substantially greater dimension than said access port, the proximal portion tapering inwardly to said distal portion to readily guide the distal tip of the instrument to said access port.

The shallow dished form of the device ensures that it lies substantially against the skin and, at the same time, minimises the possibility that the shield may inhibit the manipulation of instrumentation. The proximal portion may feature an outer upstanding rim to retain fluids which may pass from the access port, and the proximal portion may be modified to incorporate an outlet connectable to a drainage channel through which such fluids may be drained away.

At least the distal portion may be of outwardly expandable form to serve as a retractor when applied to a skin incision. In a preferred form the device is of resilient form, being adapted to be resiliently deformed from a first, relatively open configuration to a second, relatively closed configuration. When deformed into the second, relatively closed configuration the distal portion of the device may be introduced into a skin incision and released to take up its first, relatively open configuration, in so doing retracting the skin and presenting said instrument access port. This form also facilitates removal of the device as it can again be deformed after use into the second, relatively closed configuration, and after removal from the skin aperture can then be further expanded to facilitate removal from the catheter tube. The device may be of plastics material, which may be transparent to afford the user a view of the incision wound site during use.

A suitable form of this is a funnel-shaped device with a radial cut, the cut ends overlapping to provide a continuous shield in both the open and closed configurations.

Preferably the distal portion comprises at least two retractor elements such as circumferentially spaced integral lugs which act firstly to hold back the skin (ensuring that the skin cannot inadvertently contact instrumentation passed into the access port) and secondly to hold the device closely against the skin, thus leaving the user's hands free to manipulate the instrumentation.

The invention, then, provides that the operative parts of instrumentation to be introduced by way of the access port are shielded from contact with the patient's skin, thereby to inhibit transfer of micro-organisms and thus maintain a substantially sterile condition on the surface of the instrumentation. The shield can remain in position while a range of instruments are successively introduced via the access port, with a minimal risk of bacterial transfer. When serving as a retractor for a skin incision, the device of the invention fulfils simultaneously the functions of anti-contamination shield, skin retractor and instrument guide.

The invention also contemplates a vascular catheterisation kit comprising an insertion cannula such as a needle, a guidewire for intravascular application, an intravascular catheter, and a transcutaneous shield device of the type specified above. Clearly more than one of each item may be included in the kit, and indeed a range of sizes of each kit component may be provided whereby the user may select the size of each component according to the particular application. Such a kit may also incorporate one or more cutting tools, such as scalpels or scalpel blades, as well as one or more dilator tools for dilating a vascular or dermal aperture. Each component may be of one-use disposable form, or alternatively may be intended for sterilisation between uses.

According to a further aspect of the invention, there is provided a surgical technique for transcutaneous procedures, comprising the steps of:

providing an aperture in a patient's skin;

introducing into the aperture a transcutaneous shield device which presents an instrument access port;

introducing instrumentation through said access port, the shield device acting to prevent contact between the operative parts of the instrumentation and the skin as the instrumentation passes transcutaneously.

The term 'operative parts' is employed here to indicate those parts of the instrumentation which are to pass into the patient's body or which may provide an infection route into the patient's body.

The shield device may be introduced independently of other instrumentation, or it may be carried by or integral with an introducer, such as a needle, to simplify procedure.

The invention will now be described by way of example only, with reference to the accompanying figures, in which:

FIG. 1 diagrammatically illustrates a first embodiment of the invention in use;

FIG. 3 illustrates in plan view a second embodiment of the invention;

FIG. 4 shows a side view in direction A of FIG. 3;

In this description and claims, 'distal' and 'proximal' are to be read as applying to the user's (eg. the surgeon's) point of reference.

Figure 1:
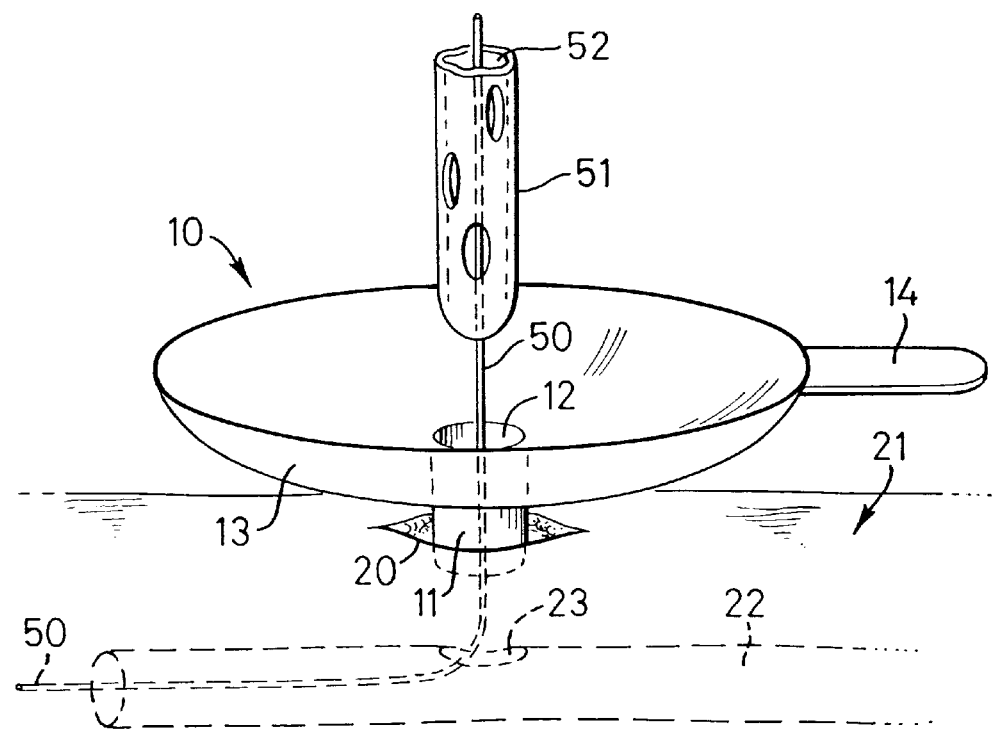
Figure 2:
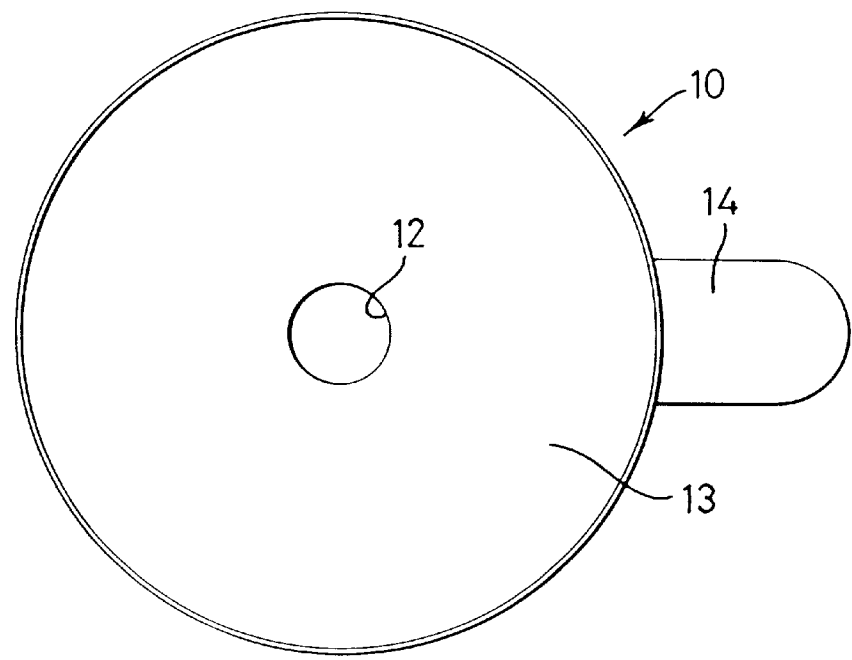
FIG. 2 shows a plan view of the device of FIG. 1.

In FIGS. 1 and 2, a shield device 10 according to the invention is shown introduced into an incision wound 20 in a patient's skin 21 during a central venous catheter insertion procedure. Preferably, the shield device 10 is introduced immediately after the incision wound 20 is made and all instruments are subsequently passed through it. The figure diagrammatically shows blood vessel 22 and guidewire 50, the guidewire being shown in place passing from the exterior through the incision and into and along the vessel 22 by way of vascular aperture 23.

The shield device 10 has a transcutaneous distal portion 11 comprising a hollow tubular element of smaller diameter than the length of the incision adapted to pass through the skin and so present an instrument access port 12. At the proximal end of this tubular element the distal portion is integrally connected to a proximal portion 13 of shallow cup form with a circular periphery and having a central circular aperture of the same diameter as the tubular element to realise the access port 12. Thus the shield device 10 is funnel-shaped and may be provided with a simple handle 14 as shown for holding in place as instrumentation is introduced during use. It is to be noted that the illustration in FIG. 1 is merely schematic, and that in use the underside of the proximal portion 13 of the device lies in fact substantially against the patient's skin.

FIG. 1 also shows the distal tip of a central venous catheter 51 having a central longitudinal lumen 52 which can be fed down guidewire 50 through the access port 12 of shield device 10 and so into vessel 22 via vascular aperture 23.

The shield device 10 serves to prevent contact between the catheter 51 and the skin 21 or the sides of the incision wound 20. As explained above, this greatly reduces the possibility of contamination passing into the patient's body. Additionally, the funnel-like shaping of the device 10 serves to aid in directing the catheter tip, as well as other instrumentation, towards the access port of the device. The shallow dished form of the proximal portion 13 ensures that the skin area surrounding the wound site is covered and provides that the shield device does not impede manipulation of the various items of instrumentation during the surgical procedure.

The modified form of the device shown in FIG. 3 has a proximal portion 113 of shallow frustro-conical form arranged to lie against the skin and present a relatively wide, shallow, dish-shaped aspect, as clearly shown in side view in FIG. 4. The shield device serves once again to aid in directing instrumentation towards access port 112. Around the outer circumference of the proximal portion 113 is an upstanding continuous rim 115 to retain blood etc. which may pass into the proximal portion 113 from the access port 112, and which may then be removed by a suction means via an outlet if desired (not shown). The shield device is formed from a substantially flat disc of material with a radial cut which is closed up by overlapping the cut edges to obtain the frustro-conical shape. The overlapping cut edges of the disc are shown in FIG. 3 as 116*a* and 116*b*, reference X representing the area of overlap. At a certain angular spacing from the cut edges 116*a* and 116*b*, two upstanding lugs 114 are provided near to the outer perimeter of the proximal portion and preferably projecting upwardly beyond upstanding rim 115 to facilitate ready manipulation by a user, who can grasp the lugs 114 with index finger and thumb respectively and squeeze them together against the resilience of the material to at least partially close up the access port 112. The purpose of this feature will be explained below. To aid in the manipulation of the device between a first, relatively open configuration and a second, relatively closed configuration, there may be provided a zone of reduced thickness 117 to provide a resilient hinging action. As FIG. 3 shows, this may be wedge shaped with sides diverging towards the outer circumference from a point close to the access port 112, and is preferably provided diametrically opposite to the overlapping edge area X.

The proximal portion 113 of the device may additionally be provided with means to allow temporary adhesion to the skin of the patient, for example, one or more adhesive strips may be provided on its distal side, or a number of small through-holes may be provided adjacent the outer periphery to enable attachment to the patient's skin by way of temporary stitches.

Figure 5:
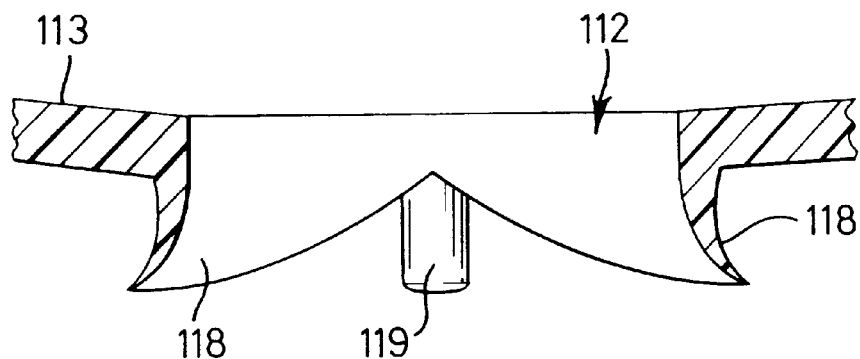
FIG. 5 shows a magnified sectional view of the central part of the device of FIG. 4 to illustrate more clearly the structural details.

As FIG. 5 shows, transcutaneous distal portion 111 comprises two downwardly and outwardly projecting shaped lips or blades 118 to act as an integral retractor, as well as at least one downwardly projecting skin peg 119. The lips 118 project downwardly from the inner circumference of the proximal portion 113 to define the sides of the access port 112, and are mutually diametrically opposed and angularly offset by about 90° from both the overlapping edge area X and from the skin peg 119. The skin peg may also be adapted to curve outwardly in a radial direction from the access port.

Figure 6:
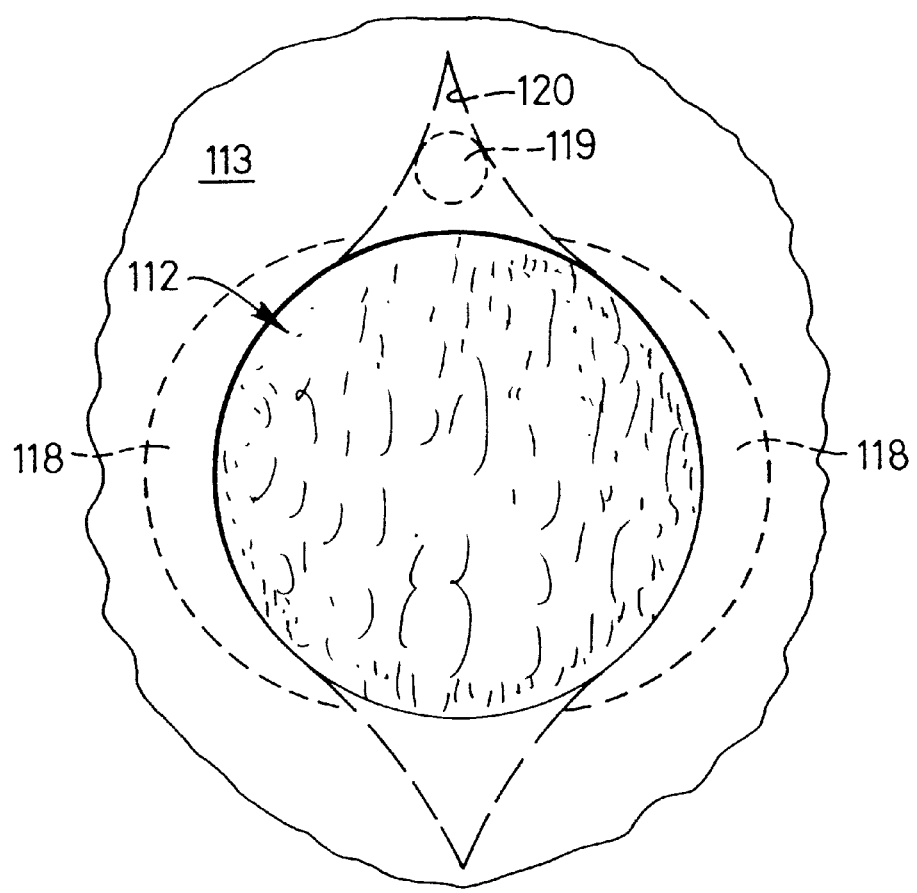
FIG. 6 shows a plan view of the central part of the device of FIG. 4.

The function of the retractor lugs and skin peg will now be described with reference to FIG. 6. Once the skin incision 120 has been made the user grasps the shield device by way of lugs 114 and squeezes it into the relatively closed configuration, so bringing the retractor lugs 118 together. The device is then lowered towards the skin and skin peg 119 is located into one end of the incision whilst retractor lugs 118 are manoeuvred under the opposed cut edges of the skin. When the device is released the retractor lugs spring apart so opening the access port 112, shielding the skin from the interior of the shield device, and holding the device firmly and closely against the skin surrounding the incision wound, thus leaving the user's hands free, and providing a stable reference platform. The action of the retractor also tends to reduce bleeding from the wound as it compresses and constricts neighbouring blood vessels. The surgical procedure can then be safely carried out as described above, and the resilient form of the device will subsequently aid in facilitating removal of the shield device. It is noted that when used with an indwelling instrument such as a central venous catheter, since the operative length of the instrument does not contact the patient's skin, it is protected from bacterial invasion during the period of use when bacteria might otherwise be able to track from the skin along the catheter surface in a longitudinal direction.

The shield device of the invention is preferably fabricated in disposable form from a semi-rigid material such as resilient plastics in a one-piece construction, or from flexible card which is preferably coated with a smooth sterilisable coating. Such materials are well suited to disposable devices as they are low cost and appropriate for fabrication on a large scale. The device, which is preferably provided to the user in a sterilised form, may be impregnated or coated with an antimicrobial agent to inhibit the growth of infectious bacteria in the wound area or in the surrounding tissue. Furthermore, as an aid to insertion through the incision wound, the external surface of the distal portion of the device may be coated with a lubricant containing an antimicrobial agent and/or a mild anaesthetic.

In the description and drawings the shield device is shown as a separate device from other components of the surgical instrumentation. However, it may alternatively be incorporated in or carried by another component. For example, the needle or other introducer may be adapted to carry the distal portion of a plastic shield device provided with retractor means, the action of withdrawing the needle when the shield device is in place releasing the retractor means to open the incision wound and allow subsequent introduction of further instrumentation.

The dimensions of the device shield are selected as appropriate for the particular application. In a typical central venous catheterisation procedure the catheter has a diameter of between 2 and 5 mm and so the internal bore of the distal portion of the shield device may therefore be of a similar or greater diameter. The outer diameter of the proximal portion substantially greater, thereby to cover a sufficiently large area of the skin to minimise as far as possible the chance of contacting the operative parts of the instrumentation with the skin. The actual diameter is open to considerable variation, but may typically be in the range 10–50 mm. As previously indicated, the invention may be realised in the form of a vascular catheterisation kit comprising one of more of each component of the kit, for example in a range of sizes to enable the user to select the size of each component according to the particular application.

The shield device may include a stopper member (not shown) to temporarily seal the access port 12, 112 for use in situations wherein the shield is to be left indwelling for a significant time period between instrument insertion procedures.

The invention has been specifically described with reference to the central venous catheterisation procedure, but clearly has application to other areas. For example, it may be employed in catheterising an intravascular location for temporary feeding of a patient who has undergone major abdominal surgery.

What is claimed is:

1. A transcutaneous shield device for insertion into a skin aperture, comprising a transcutaneous distal portion providing an instrument access port which allows insertion of an instrument, the distal portion being connected to an external proximal portion of shallow dish-shaped form of substantially greater dimension than said access port, said dimension being sized to prevent intrusion of the proximal portion into said skin aperture such that said proximal portion provides a shield between an instrument and a skin, the proximal portion tapering inwardly to said distal portion to readily guide a distal tip of the instrument to said access port.

2. A device according to claim 1, wherein the proximal portion is provided with an outer upstanding rim to retain fluids which may pass from the access port.

3. A device according to claim 2, the proximal portion incorporating an outlet connectable to a drainage channel through which such fluids may be drained away.

4. A device according to claim 1, wherein at least the distal portion is of outwardly expandable form to serve as a retractor when applied to a skin incision.

5. A device according to claim 4, wherein at least the distal portion is formed of a resilient material such that the distal portion is resiliently deformable from a first, relatively open, configuration to a second, relatively closed, configuration.

6. A device according to claim 5, wherein the proximal portion has a funnel-shaped form with a radial cut defined by cut ends in the funnel-shaped form, the cut ends overlapping to provide a continuous shield in both the first relatively open and second relatively closed configurations.

7. A device according to claim 4, wherein the distal portion comprises at least two circumferentially spaced retractor lugs.

8. A device according to claim 1 being fabricated, at least in part, from transparent plastics material.

9. A vascular catheterisation kit comprising an insertion cannula such as a needle, a guidewire for intravascular application, an intravascular catheter, and a transcutaneous shield device according to claim 1.

10. A surgical technique for transcutaneous procedures, comprising the steps of:

providing an aperture in a patient's skin;

introducing into the aperture a transcutaneous shield device providing an instrument access port, said transcutaneous shield device having an external portion of such dimension to prevent intrusion of the external portion into said skin aperture;

introducing operative parts of instrumentation through said access port, the shield device acting to prevent contact between the operative parts of the instrumentation and the skin as the instrumentation passes transcutaneously.

11. A technique according to claim 10, whereby the shield device is carried by, or integral with, an introducer, such as a needle, to simplify the introduction of said shield device.

\* \* \* \* \*